United States Patent
Verzal et al.

(10) Patent No.: US 11,357,991 B2
(45) Date of Patent: Jun. 14, 2022

(54) MEDICAL ELEMENT INSERTION POSITION INDICATOR

(71) Applicant: INSPIRE MEDICAL SYSTEMS, INC., Golden Valley, MN (US)

(72) Inventors: Kevin Verzal, Golden Valley, MN (US); John Rondoni, Golden Valley, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 94 days.

(21) Appl. No.: 16/474,792

(22) PCT Filed: Jun. 1, 2018

(86) PCT No.: PCT/US2018/035570
§ 371 (c)(1),
(2) Date: Jun. 28, 2019

(87) PCT Pub. No.: WO2018/222973
PCT Pub. Date: Dec. 6, 2018

(65) Prior Publication Data
US 2019/0351239 A1    Nov. 21, 2019

Related U.S. Application Data

(60) Provisional application No. 62/514,354, filed on Jun. 2, 2017.

(51) Int. Cl.
*A61N 1/372* (2006.01)
*A61N 1/362* (2006.01)
*A61N 1/375* (2006.01)
*A61B 34/20* (2016.01)

(52) U.S. Cl.
CPC ............ *A61N 1/3752* (2013.01); *A61B 34/20* (2016.02); *A61N 1/362* (2013.01); *A61N 1/37211* (2013.01)

(58) Field of Classification Search
CPC .. A61N 1/3752; A61N 1/362; A61N 1/37211; A61B 34/20
See application file for complete search history.

(56) References Cited

U.S. PATENT DOCUMENTS

| 5,645,577 A | 7/1997 | Froberg et al. |
| 5,683,433 A | 11/1997 | Carson |
| 5,766,042 A * | 6/1998 | Ries ...................... H01R 24/28 439/668 |
| 6,044,302 A | 3/2000 | Persuitti et al. |

(Continued)

FOREIGN PATENT DOCUMENTS

EP    1625875    2/2006

*Primary Examiner* — Carl H Layno
*Assistant Examiner* — Anh-Khoa N Dinh
(74) *Attorney, Agent, or Firm* — Dicke, Billig & Czaja, PLLC

(57) ABSTRACT

An electronic medical device includes a first portion, with the first portion including a first insertion hole and an external surface. The first insertion hole is to removably receive an elongate element. The external surface of the first portion comprises a first position indicator, which is located to be visibly juxtaposed relative to a first operative element of the elongate element when the elongate element is fully inserted in the first insertion hole. In some instances, the position indicator may serve a dual function as a vent.

24 Claims, 12 Drawing Sheets

(56) References Cited

U.S. PATENT DOCUMENTS

| | | | |
|---|---|---|---|
| 6,112,121 A * | 8/2000 | Paul | A61N 1/3752 |
| | | | 607/36 |
| 6,192,276 B1 | 2/2001 | Strandberg | |
| 6,672,895 B2 | 1/2004 | Scheiner | |
| 7,983,754 B2 | 7/2011 | Kessler et al. | |
| 8,600,508 B2 | 12/2013 | Majewski et al. | |
| 9,682,226 B2 | 1/2017 | Verzal et al. | |
| 2003/0163171 A1 * | 8/2003 | Kast | A61N 1/3752 |
| | | | 607/36 |
| 2004/0122481 A1 | 6/2004 | Tidemand et al. | |
| 2006/0020314 A1 | 1/2006 | Bodner | |
| 2006/0030204 A1 * | 2/2006 | Jones | A61N 1/3752 |
| | | | 439/488 |
| 2007/0049985 A1 * | 3/2007 | Kessler | H01R 13/641 |
| | | | 607/37 |
| 2008/0071313 A1 * | 3/2008 | Stevenson | A61N 1/3752 |
| | | | 607/2 |
| 2009/0018601 A1 * | 1/2009 | Deininger | A61N 1/3752 |
| | | | 607/37 |
| 2009/0248124 A1 | 10/2009 | Pianca et al. | |
| 2010/0137929 A1 * | 6/2010 | Libbey | A61N 1/3752 |
| | | | 607/5 |
| 2010/0249869 A1 * | 9/2010 | Ries | A61N 1/3752 |
| | | | 607/37 |
| 2011/0004124 A1 * | 1/2011 | Lessar | A61N 1/3605 |
| | | | 600/587 |
| 2011/0071593 A1 * | 3/2011 | Parker | A61N 1/36021 |
| | | | 607/46 |
| 2015/0094791 A1 | 4/2015 | Edgell et al. | |
| 2015/0157853 A1 * | 6/2015 | Verzal | A61N 1/36021 |
| | | | 607/46 |

\* cited by examiner

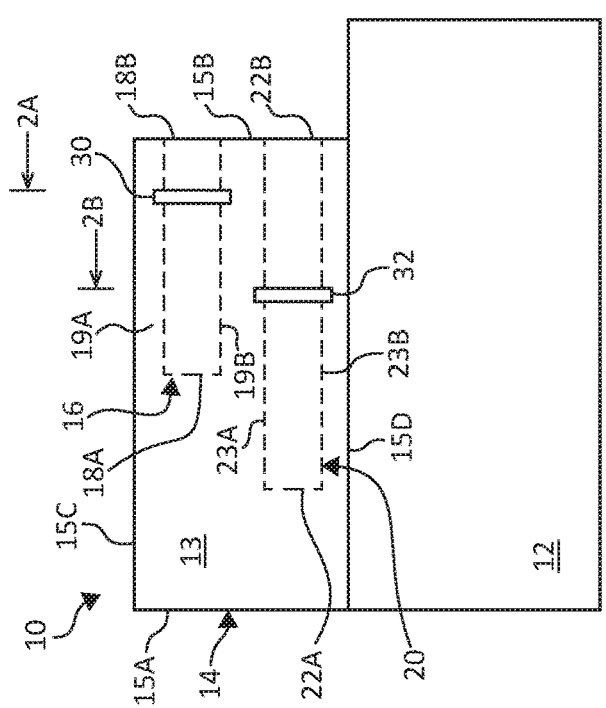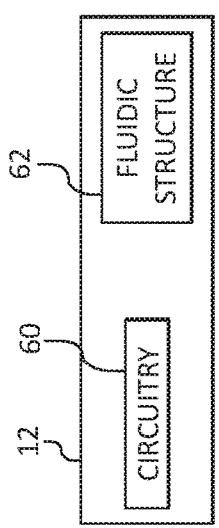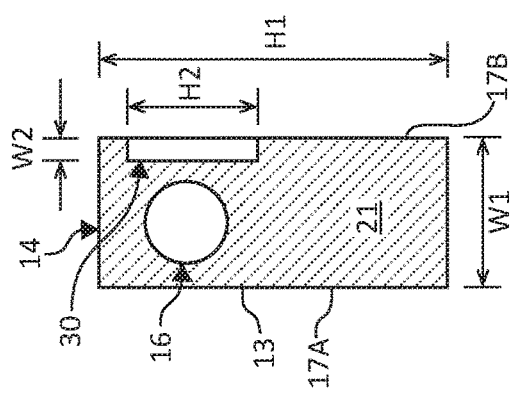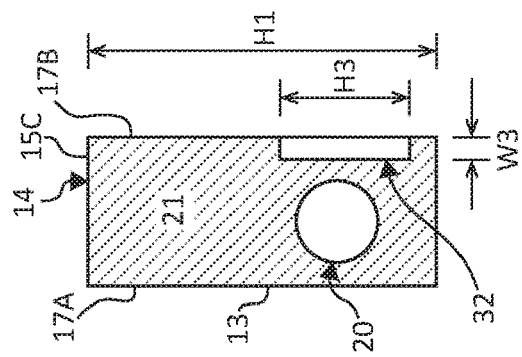

541

540 — ARRANGING THE MEDICAL DEVICE AS AN ELECTRONIC MEDICAL DEVICE AND THE ELONGATE ELEMENT AS AM ELECTRICALLY CONDUCTIVE LEAD SUCH THAT THE FULL INSERTION OF THE LEAD INTO THE INSERTION HOLE ESTABLISHES AT LEAST ELECTRICAL COMMUNICATION BETWEEN THE ELECTRONIC MEDICAL DEVICE AND THE ELECTRICALLY CONDUCTIVE LEAD

FIG. 13A

550 — ARRANGING THE ELECTRONIC MEDICAL DEVICE AS A MONITORING DEVICE AND THE LEAD AS A SENSING LEAD

FIG. 13B

560 — ARRANGING THE ELECTRONIC MEDICAL DEVICE AS A STIMULATION DEVICE AND THE LEAD AS A STIMULATION LEAD

FIG. 13C

570 — ARRANGING THE MEDICAL DEVICE AS A FLUID DELIVERY DEVICE AND THE ELONGATE ELEMENT AS A CATHETER SUCH THAT FULL INSERTION OF THE CATHETER INTO THE INSERTION HOLE ESTABLISHES AT LEAST FLUID COMMUNICATION BETWEEN THE FLUID DELIVERY DEVICE AND THE CATHETER

602 — ARRANGING A VENT BETWEEN AN INSERTION HOLE IN A FIRST PORTION OF A MEDICAL DEVICE AND APERTURE AT THE EXTERNAL SURFACE OF THE FIRST PORTION

FIG. 14

604 — FORMING AT LEAST THE APERTURE OF THE VENT AS PART OF A FIRST POSITION INDICATOR ON THE EXTERNAL SURFACE OF THE FIRST PORTION OF THE MEDICAL DEVICE

FIG. 15

610 — FORMING THE VENT AS DIRECT INTERSECTION BETWEEN AN INSERTION HOLE OF THE FIRST PORTION OF THE MEDICAL DEVICE AND AN APERTURE, WHICH FORMS PART OF A FIRST POSITION INDICATOR ON THE EXTERNAL SURFACE OF THE FIRST PORTION

FIG. 16

615 — FORMING THE VENT AS A CONDUIT EXTENDING FROM AN INSERTION HOLE WITHIN A FIRST PORTION OF AN MEDICAL DEVICE TO AN APERTURE, WHICH FORMS PART OF A FIRST POSITION INDICATOR ON THE EXTERNAL SURFACE OF THE FIRST PORTION

FIG. 17

620 — LOCATING THE VENT WITHIN A PREDETERMINED DISTANCE FROM A CLOSED END OF THE INSERTION HOLE

FIG. 18

625 — LOCATING A VENT PROXIMAL TO A SEALING ZONE WITHIN THE INSERTION HOLE

FIG. 19

630 — LOCATING A VENT DISTAL TO A SEALING ZONE WITHIN THE INSERTION HOLE

FIG. 20

635 — ARRANGING THE VENT TO INCLUDE A ONE-WAY FLOW ELEMENT

FIG. 21

640 — FORMING THE FIRST POSITION INDICATOR TO HAVE THE SAME COLOR AS THE TRANSLUCENT MATERIAL FROM WHICH THE FIRST PORTION IS FORMED

FIG. 22

645 — FORMING THE FIRST POSITION INDICATOR SOLELY BY AN ABSENCE OF, OR AN ADDITION OF, THE SAME MATERIAL FROM WHICH THE FIRST PORTION WAS FORMED

FIG. 23

MEDICAL ELEMENT INSERTION POSITION INDICATOR

CROSS-REFERENCE TO RELATED APPLICATIONS

This 35 U.S.C. § 371 National Phase application claims priority to International Application No. PCT/US18/35570, filed Jun. 1, 2018, which claims the benefit of U.S. Provisional Patent Application No. 62/514,354, filed Jun. 2, 2017; which are both incorporated herein by reference in their entirety.

BACKGROUND

Many medical devices include electronic components and may be associated with conductive leads connectable to the medical device. Some leads are removably insertable into a portion of the medical device to establish both an electrical and a mechanical connection.

BRIEF DESCRIPTION OF THE DRAWINGS

FIG. 1A is a side plan view schematically representing an example medical device.

FIG. 1B is a block diagram schematically representing an example main portion of a medical device.

FIGS. 2A-2B are each an enlarged partial sectional view of a first portion of an example medical device.

FIGS. 13A-13C are each a flow diagram schematically representing an example method involving an electronic medical device and electrically conductive lead.

FIG. 13D is a flow diagram schematically representing an example method involving a fluid delivery device and catheter.

FIGS. 14-21 are each a flow diagram schematically representing an example method involving a vent associated with an insertion hole of a first portion of a medical device.

FIGS. 22-23 are each a flow diagram schematically representing an example method regarding formation of a position indicator for insertion of an elongate element.

DETAILED DESCRIPTION

Figure 3:
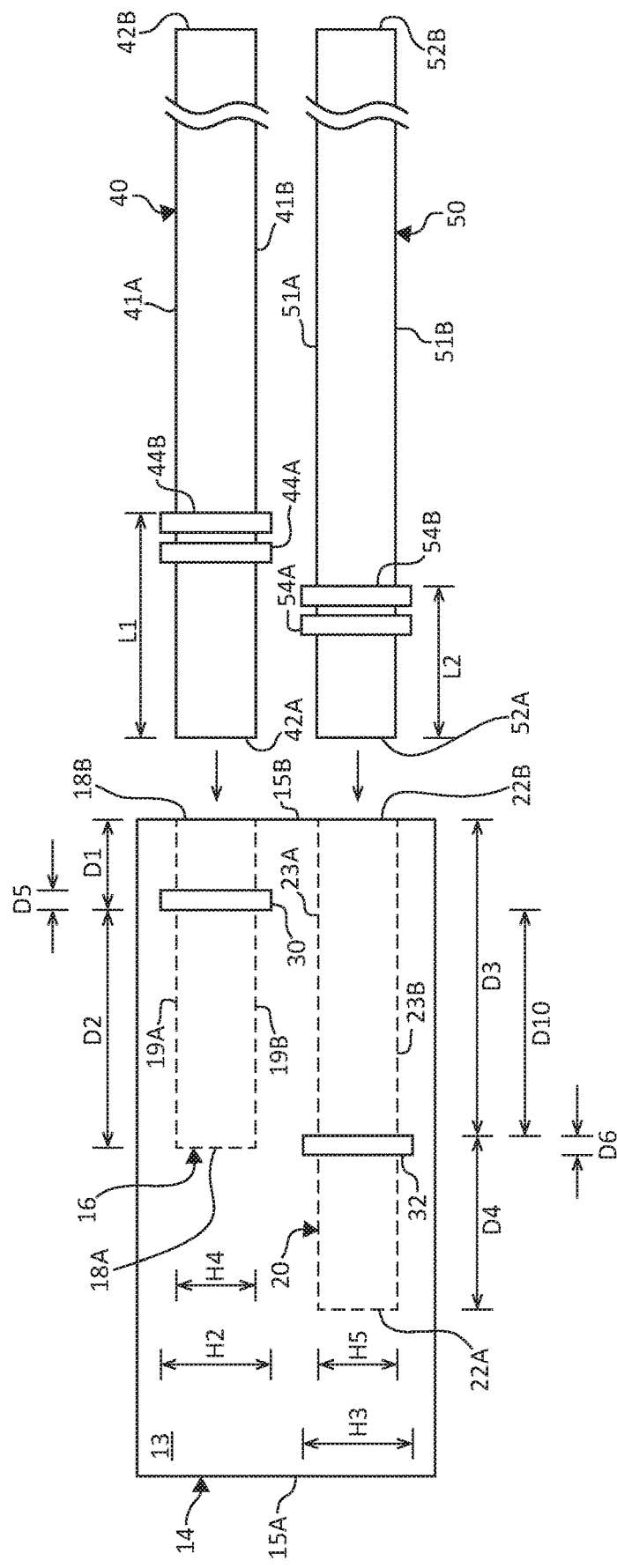
FIG. 3 is a side plan view schematically representing an example medical device and an example elongate element for insertion into a portion of the example medical device.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure relate to providing confirmation of proper insertion of a medical elongate element into an insertion hole within a first portion (e.g. header or other) of a medical device. In some examples, such confirmation may be performed as part of a method of implanting the medical device and/or the medical elongate element within a patient's body. In particular, many implantation procedures preclude securing an implantable elongate element to an implantable medical device prior to implantation because tunneling and positioning of the respective implantable elements cannot be performed adequately if the respective implantable elements were already connected prior to initiating implantation. Accordingly, at least some examples of the present disclosure facilitate confirmation of proper connection of the respective implantable elements (e.g. elongate element and medical device) after tunneling and/or positioning of the respective implantable elements has been substantially completed. Confirming proper insertion may ensure robust mechanical, electrical, and/or fluidic connection during the implanted life cycle of the implantable elements. In some instances, such proper insertion may sometimes be referred to as a complete insertion or full insertion.

In some examples, a position indicator is formed on an external surface of the first portion, which may be translucent, to enable observing a position of the medical elongate element during insertion relative to the position indicator. In some examples, the position indicator may comprise a recess, a protrusion, or other topographic feature and omits color in some examples. In some examples, more than one position indicator may be provided for each insertion hole. In some examples, the first portion of the medical device may comprise a plurality of insertion holes (e.g. 2, 3, 4, etc.) and associated position indicators. In some examples, the medical device may comprise an electronic medical device, which includes electronic circuitry and/or is supported by external electronic circuitry. In some examples, the medical device may comprise a non-electronic medical device which omits electronic circuitry and/or operates without the support of electronic circuitry.

In some examples, insertion of the medical elongate element into the insertion hole of the medical device may result in a mechanical connection, an electrical connection, and/or a fluid connection between the medical elongate element and the medical device. In some such examples, the mechanical connection may comprise an electrically non-conductive material arranged to electrically insulate an electrical connection (between the medical device and the medical elongate element) from the external environment, fluids, other electrically conductive elements, etc.

In some examples the medical elongate element may comprise a lead including electrically conductive element and the medical device may comprise an electronic medical device such that insertion of the lead into the insertion hole results in an electrical and mechanical connection between the lead and the medical device.

In some examples, the medical elongate element may comprise a catheter including at least one lumen for fluid flow and the medical device may comprise a fluid delivery device such that insertion of the catheter into the insertion hole of the fluid delivery device results in at least a mechanical and a fluidic connection between the medical device and the catheter. In some such examples, the fluid delivery device may comprise a drug delivery device. In some such examples, insertion of the catheter into the insertion hole of the fluid delivery device also may comprise an electrical connection in addition to the mechanical and fluidic connection.

In some examples, a vent may be formed as part of a position indicator with the vent establishing fluid communication between the insertion hole and environment external to the first portion of the medical device. In one aspect, the vent or vents may act as a gas (e.g. air) pressure relief during insertion of the medical elongate element into the insertion hole, thereby easing insertion of the medical elongate element and/or thereby enhancing robust retention of the medical elongate element in the insertion hole. In some examples, forming the vent as part of the position indicator may simplify establishing the vent, such as but not limited to when the position indicator comprises a recess.

These examples, and additional examples, will be further described and/or illustrated in association with FIGS. 1A-27.

FIG. 1A is side plan view schematically representing an example medical device 10, which may comprise an implantable pulse generator (IPG) 10 in some examples. In some examples, the medical device 10 may comprise a monitor, a diagnostic device, a therapy management device, a communication device, drug delivery device, etc., each of which may be implantable or non-implantable. Some such medical devices may comprise an electronic medical device (e.g. pulse generator, other) while some such medical devices may non-electronic in the sense that they omit electronic circuitry and/or may not be supported via external electronic circuitry. Accordingly, while the medical device 10 may comprise any one, or a combination of, different types of medical devices, it will be understood that for illustrative and descriptive simplicity, the following description relates to an implantable pulse generator. However, at least some of the features, attributes, and principles associated with the implantable pulse generator 10 as described herein may also be incorporated within any one, or a combination of, the different types of above-described medical devices other than an implantable pulse generator.

As shown in FIG. 1A, the IPG 10 comprises a main portion 12 and a header 14. The main portion 12 may comprise a biocompatible casing to house circuitry and/or other components for delivering neurostimulation therapy, sensing physiologic data, monitoring/evaluating therapy, monitoring/evaluating patient/health, etc. In some examples, the IPG 10 may comprise an IPG for treating sleep disordered breathing (SDB), such as but not limited to obstructive sleep apnea. In some examples, the IPG 10 may comprise an IPG for treating other diseases, physiologic conditions, etc.

As shown in FIG. 1B, in some examples main portion 12 may comprise circuitry 60 in some examples as described above regarding FIG. 1A. However, in some examples main portion 12 in FIGS. 1A-1B may omit circuitry 60. In some examples, circuitry 60 may comprise the components, functions, properties and/or support the components, functions, and properties described above for main portion 12 as described above in association with FIG. 1A. As further shown in FIG. 1B, in some examples main portion 12 may comprise a fluidic structure 62 to supply fluid to an elongate element connectable to the main portion 12 via header 14, or to receive fluid from an elongate element connectable to the main portion 12 via header 14. Accordingly, it will be understood that fluidic structure 62 may comprise fluidic pathways extending between the main portion 12 and header 14 to facilitate fluidic communication between the main portion 12 and any catheters connected via header 14. In some examples, the fluidic structure 62 includes a reservoir to store fluids. In some examples, main portion 12 may comprise circuitry 60 and fluid reservoir 62. In some examples, fluidic structure 62 may comprise a pump to move fluids into and through an elongate element 40, 50 connected to the main portion 12 via first portion 14 (e.g. header). In some such examples, the supplying or reception of fluids via fluidic structure 62 may be at least partially controlled via the components, functions, properties associated with circuitry 60, such as but not limited to a controller.

In general terms, header 14 is configured to removably, securely receive one or more leads (e.g. 40, 50 in FIG. 3) and to provide for electrical connection between such leads 40, 50 and circuitry (and/or other components) within the main portion 12 of the IPG 10. As shown in FIG. 1A, header 14 comprises an external surface 13 and is defined by opposite ends 15A, 15B, a top 15C, a bottom 15D, opposite sides (17A, 17B in FIGS. 2A-2B). Each insertion hole 16 and 20 (shown in dashed lines) defines an elongate aperture through a portion of a body 21 of header 14 and are configured to receive insertable distal end portions of leads (40, 50 in FIG. 3). While not shown for illustrative simplicity, it will be understood that the insertion holes 16, 20 include and/or are in communication with electrical contacts/connectors for establishing electrical connection between the leads 40, 50 and the circuitry within main portion 12 of IPG 10.

As shown in FIG. 1A, in some examples insertion hole 16 includes closed end 18A and opposite open end 18B at end 15B of header 14, as well opposite side walls 19A, 19B. Meanwhile, insertion hole 20 includes closed end 22A and opposite open end 22B, as well as opposite side walls 23A, 23B. In some instances, each respective hole 16, 20 may sometimes be referred to as a slot, cavity, pocket, bore, etc., which defines an aperture having a closed end and opposite open end.

Because the body 21 of the header 14 is translucent and/or transparent, the insertion holes 16, 20 are visible to the naked eye despite their interior location. Moreover, the insertion of a lead (e.g. 40, 50) into and through the holes 16, 20 would be visible as well, thereby enabling a determination with the naked eye of the relative depth of insertion of the lead 40, 50 into their respective insertion holes 16, 20.

As further shown in FIG. 1A, in some examples header 14 also comprises a lead insertion position indicator 30 and/or a lead insertion position indicator 32. In at least some examples, the position indicators 30, 32 may facilitate determining whether a lead (40, 50 in FIGS. 3-4) has been fully inserted into the respective insertion holes 16, 20.

In some examples, the terms "full insertion", "fully inserted", "complete insertion", etc. may sometimes be used to refer to an elongate element being inserted within an insertion hole (e.g. 16, 20) sufficiently to ensure a robust, secure mechanical connection and to establish a reliable electrical connection and/or reliable fluidic connection. In some such examples, these terms may also refer to instances in which the elongate element also has been inserted such that a proximal end of the elongate element makes contact with a closed end of the insertion hole (e.g. 16, 20). However, it will be understood that in some examples, a full insertion or complete insertion of an elongate element may not involve the proximal end of the elongate element contacting the closed end of the insertion hole (e.g. 16, 20) provided that a robust, secure mechanical, electrical, and/or fluidic connection has been established between the elongate element and the medical device within the insertion hole (e.g. 16, 20).

In some examples, each lead insertion position indicator 30, 32 may extend in a position transverse to a longitudinal axis of each insertion hole 16, 20, respectively. As further later described in FIGS. 3-4, in at least some examples each lead insertion position indicator 30, 32 may be located a different distance (D1, D3) relative to the end 15B of header 14. In some instances, such arrangements may sometimes be referred to as the different indicators 30, 32 having respectively different axial positions on the header 14.

However, in some examples, the different position indicators 30, 32 may have the same axial position relative to the end 15B of header 14. Stated differently, each position indicator 30, 32 may be located at the same distance (either D1 or D3 or some other distance) away from end 15B of header 14.

As further shown in the sectional views of FIGS. 2A, 2B, each indicator 30, 32 is formed on and/or within the external surface 13 of header 14 and does not interfere with the respective insertion holes 16, 20. Indicator 30 has a height H2, which forms a fraction of the full height H1 of header 14. In some examples, the height H2 may be less than one-half of the full height H1. In some examples, the height H2 may be less than one-third of the full height H1. In some examples, the height H2 may be less than one-fourth of the full height H1. Indicator 32 has a height H3, which forms a fraction of the total height H1 of header 14. In some examples, the height H3 of indicator 32 may exhibit relationships (e.g. one-half, one-third, one-fourth, etc.) relative to full height H1 of header 14 in a manner similar to height H2 of indicator 30.

In some examples, height H2 of indicator 30 is substantially equal to height H3 of indicator 32. However in some examples, the heights H2, H3 may differ from each other. In some examples, this difference may facilitate differentiating the purpose/function of the respective insertion holes 16, 20 and/or serve other purposes.

In some examples, each indicator 30, 32 (FIGS. 2A, 2B) forms a groove or recess having a depth (W2, W3) extending inward into the body 21 of header 14 from the external surface 13 with the header 14 having a full width W1 extending between opposite sides 17A, 17B. In some examples, the depth (W2, W3) is less than at least one-quarter of the full width (W1) of header 14. In some examples, the depth (W2, W3) is less than one-tenth of the full width (W1) of header 14. When combined with the relatively short length (H2, H3) and the relatively small width (D5, D6 in FIG. 3) of the respective indicators 30, 32, such arrangements pose virtually no impact on the structural integrity of the header 14. Such example arrangements of the present disclosure stand in sharp contrast to some commercially available arrangements which remove relatively large portions of material (via a bore) from a body of a header in order to implement a position indicator and/or which involve insertion of replacement material into the bore or cavity created from such removal. Moreover, by avoiding the use of insertion materials, the example arrangements of the present disclosure may eliminate the possibility of dislodgement of insertion materials and/or avoid new biocompatibility concerns.

In addition, in at least some examples of the present disclosure in which at least two separate position indicators 30, 32 have different axial positions (as described above and as shown in the FIGS), such arrangements may avoid the formation of multiple interior bores into a body of the header (in addition to lead insertion holes) as might occur in some commercially available "position-indicator" arrangements if multiple indicators were implemented with different axial positions. Such multiple, indicator interior bore arrangements in commercially available headers may further comprise the structural integrity of a header.

In some examples, at least one of the respective position indicators 30, 32 may comprise a protrusion instead of a recess (shown in FIGS. 2A-2B). In some examples, both of the position indicators 30, 32 may comprise a protrusion, respectively. In some examples, one of the position indicators 30, 32 comprises a protrusion while the other respective one of the position indicators comprises a recess. In some such arrangements, the presence of a recess and/or protrusion forming a position indicator may facilitate tactile feedback by the operator to quickly and assuredly identify the position on the header 14. Moreover, in some instances based on such tactile feedback, the operator may gauge the position of the inserted lead relative to the finger-sensed position of the indicator 30 and/or 32. In some such arrangements in which one indicator 30 or 32 comprises a recess and the other indicator (30 or 32) comprises a protrusion, such an arrangement may enable the operator to employ tactile senses to differentiate the holes 16, 20 from each other for insertion of different leads 40, 50.

Moreover, because the respective indicators 30, 32 are physically independent and separate of each other (in at least some examples), such arrangements may significantly minimize removal of material from body 21 of header 14 unlike some commercially available arrangements which utilize a single bore extending from a top of a header to the bottom of the header.

In addition, in at least some examples of the present disclosure which utilize a relatively shallow depth, narrow width, and short height for each position indicator, such arrangements facilitate a high degree of flexibility in placing the respective position indicators 30, 32 in different locations on the header 14, unlike some commercially available arrangements which employ a single bore to act as an indicator for multiple insertable leads.

In some examples, by forming the position indicators 30, 32 on the external surface 13 and external to the insertion holes 16, 20, the position indicators 30, 32 remain visible even during and/or after full insertion of leads 40, 50 (FIGS. 3-4) into the respective holes 16, 20). In some examples, such arrangements may overcome a temptation to use color and/or other additional means to facilitate confirmation of proper insertion of the leads 40, 50.

Stated differently, in at least some examples, the position indicators 30, 32 are at least primarily defined by an absence of material (e.g. a recess or groove) at the external surface 13 of header 14 and/or at primarily defined by a protrusion of a portion of the body 21 of header 14 relative to the surrounding portions of the external surface 13 of header 14. Accordingly, in such examples, the position indicators 30, 32 do not include any color other than the color intrinsic to the material forming the body 21 of the header 14. With this in mind, in the at least some examples in which the body 21 of header 14 is translucent or transparent, the position indicators 30, 32 would be transparent or translucent.

With further reference to at least FIGS. 2A-2B, in some examples in which both position indicators 30, 32 are present, they can be located on opposite sides (e.g. 17A, 17B) of the header 14. In such arrangements, the respective position indicators 30, 32 may have the same general location (e.g. distance from end 15B or other reference on header 14) or the respective position indicators 30, 32 may have different locations (e.g. distance from end 15B or other reference on header 14)

Moreover, in some examples in which just one position indicator is present on header 14, the position indicator can be on either side 17A or 17B of header 14.

As further shown in FIG. 3, each respective insertable lead 40, 50 extends between a distal end (42A, 52A, respectively) and opposite proximal end (42B, 52B, respectively). In some examples, insertable lead 40 may comprise at least one seal structure, such as seals 44A, 44B, which are closer to distal end 42A than proximal end 42B. In some examples, the at least one seal 44A, 44B may comprise an O-ring or other sealing structure. In some examples, the at least one seal 44A, 44B also serves additional functions, such as providing a marker regarding the location of the distal end of the insertable lead relative to the hole 16 of the header 14.

In some examples, it is solely the structure/form provided by the at least one seal 44A, 44B which provides the marker/location identification function. Stated differently, in at least some examples an intrinsic color or other attribute of the at least one seal 44A, 44B does not provide the visible marker function.

In some examples, instead of the at least one element 44A, 44B providing a sealing function, elements 44A, 44B may comprise solely a marker/location identification function.

In some examples, the at least one element 44A, 44B may comprise any visible portion of a distal portion of lead (40, 50), whether such element(s) 44A and/or 44B takes the form of a recess, a protrusion, conspicuous surface appearance, etc. and/or whether such element(s) 44A and/or 44B already performs a function (e.g. seal, electrode, radiopaque marker, etc.) other than or in addition to being a lead insertion position marker. With this in mind, it will be understood that in at least some examples, an already existing feature (e.g. seal, metal electrode/contact, etc.) of a header-insertion portion of a lead may be used without structural modification and/or without visual modification in comparison to position indicators 30, 32 to indicate the relative depth of insertion of the lead 40, 50 within the insertion holes 16, 20 of the header 14.

Figure 4:
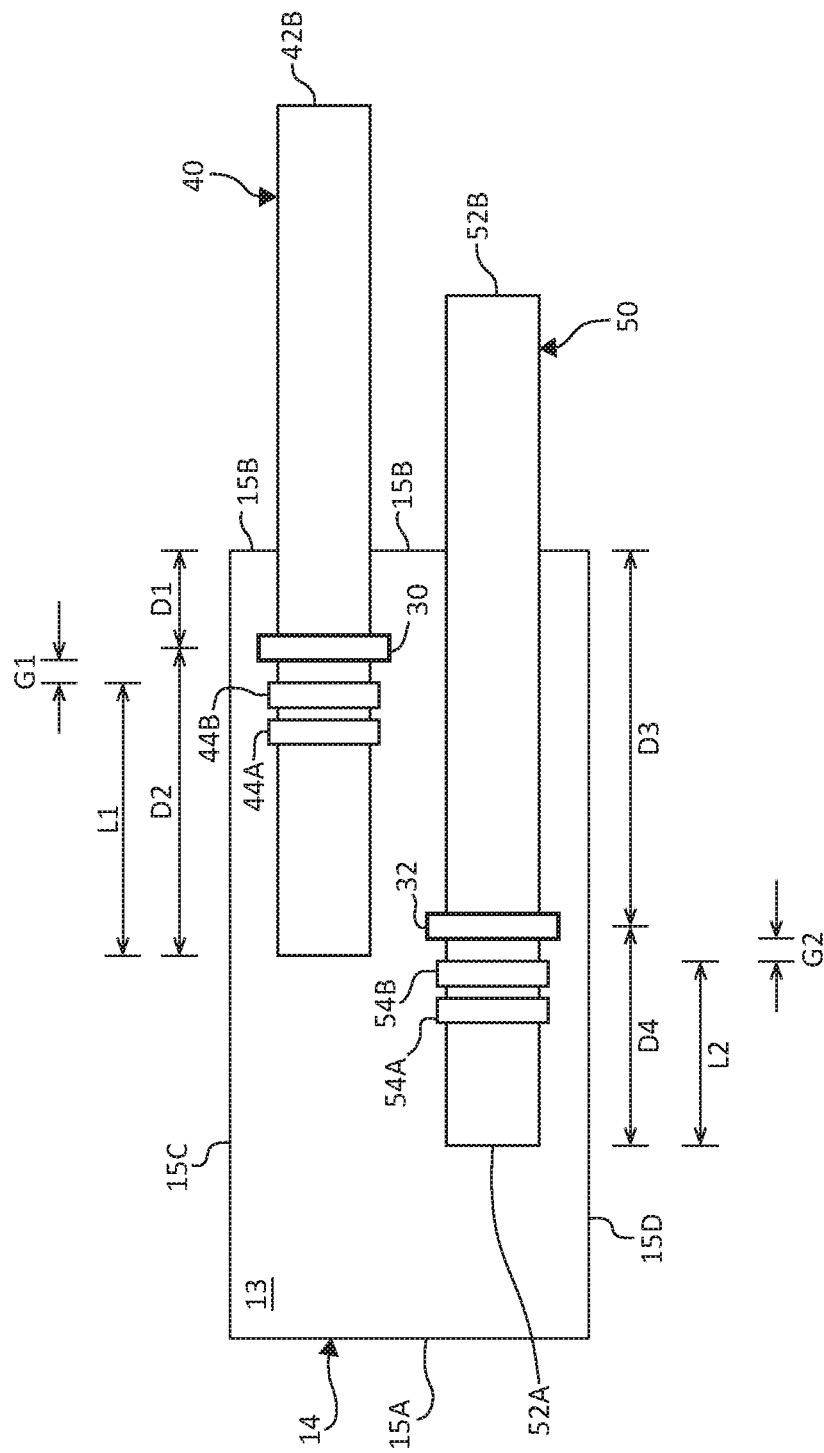
FIG. 4 is a side plan view schematically representing an example medical device with the example elongate element of FIG. 3 inserted into a portion of the example medical device.

In some examples, the at least one seal 44A, 44B is located a first distance L1 from the distal end 42A of lead 40. As shown in FIGS. 3-4, the first distance L1 is less than a distance D2 of position indicator 30 from the closed end 18A of insertion hole 16 such that upon full insertion of lead 40 into hole 16, the at least one seal 44A, 44B will be distal to the position indicator 30, as shown in FIG. 4.

In some examples, lead 50 comprises at least one seal 54A, 54B having at least some of substantially the same features as the at least one seal 44A, 44B of lead 40. In some examples, the at least one seal 54A, 54B is located a second distance L2 from the distal end 52A of lead 50. As shown in FIGS. 3-4, the second distance L2 is less than a distance D4 of position indicator 32 from the closed end 22A of insertion hole 20 such that upon full insertion of lead 50 into hole 16, the at least one seal 54A, 54B will be distal to the position indicator 32, as shown in FIG. 4.

In some examples, position indicator 30 is located a distance D1 from the end 15B of header 14 while position indicator 32 is located a distance D3 from end 15B. In some examples, the distance D3 differs from distance D1, such as being greater than D1 resulting in a distance (D10 in FIG. 3) between the respective position indicators 30, 32. In some examples, such arrangements may facilitate confirming the relative insertion of and/or fully inserted position of each respective lead 40, 50 because the respective indicators 30, 32 are clearly separate from each other. Moreover, in some examples, such arrangements may facilitate a quick visual guide regarding which lead 40, 50 should be inserted in which insertion hole 16, 20.

As shown in FIG. 3, in some examples the insertion hole 16 has a diameter H4 which is slightly less than the height H2 of indicator 30, while the insertion hole 20 has a diameter H5 which is slightly less than the height H3 of indicator 32. In some examples, the respective heights H2, H3 of the indicators 30, 32 may be equal to or less than the respective diameters H4, H5 of insertion holes 16, 20.

FIG. 4 is a side plan view schematically representing leads 40, 50 being fully inserted within the respective insertion holes 16, 20 of header 14. As previously described in such arrangements, the at least one position indicator (44A, 44B for lead 40; 54A, 54B for lead 50) is distal to the respective position indicator (30 of header 14; 32 of header 14).

In some examples, as shown in FIG. 4, upon full insertion of lead 40 into insertion hole 16 of header 12, a gap G1 is present between at least one seal 44A, 44B and the indicator 30. In some examples, gap G1 may facilitate confirmation of the full insertion of lead 40 into header 14.

In some examples, as shown in FIG. 4, upon full insertion of lead 50 into insertion hole 20 of header 14, a gap G2 is present between at least one seal 54A, 54B and the indicator 32. In some examples, gap G2 may facilitate confirmation of the full insertion into header 14.

It will be understood that in some examples, one indicator 30 may be present for hole 16 while header 14 omits an indicator (e.g. 32) for hole 20, or vice versa. However, in some examples, header 14 implements both indicators 30, 32.

In some examples, position indicators 30, 32 may be implemented on both sides 17A, 17B of header 14 such that the header 14 has a total of four position indicators, with two position indicators (one indicator 30, and one indicator 32) on side 17A and two position indicators (one indicator 30, and one indicator 32) on opposite side 17B. In some such arrangements, the position indicator 30 has the same axial position on both sides 17A, 17B and each position indicator 32 has the same axial position on both sides 17A, 17B. Via such arrangements, the operator may utilize whichever position indicator 30, 32 is most convenient, whether by tactile feel and/or by visible observation.

In at least some examples, the position indicators 30, 32 may be implemented at little or no incremental manufacturing cost, development costs, etc. In at least some examples, the position indicators 30, 32 may be implemented without introducing new biocompatibility concerns and/or may be implemented without testing of new materials and/or colors. In at least some examples, the position indicators 30, 32 may present little or no interruption of overall lead visualization.

It will be understood that in some examples that the plurality of insertion hole shown in FIGS. 1A-4 within header 14 may comprise a great number (e.g. 3, 4, etc.) of insertion holes than the two separate insertion holes (e.g. 16, 20), with at least one position indicator uniquely associated with each respective, different insertion hole of the plurality of insertion holes. In some examples, some insertion holes may omit a position indicator as desired.

However, in some examples, a header 14 may comprise a single insertion hole and associated position indicator (e.g. 30 or 32).

In some examples, the previously described at least one element 44A, 44B (and/or MA, 54B) may provide structures and/or functions in addition to, or instead of, a seal. Accordingly, in some examples, the at least one element 44A, 44B (and/or MA, MB) may sometimes be referred to as an operative element or first operative element.

With this in mind, in some examples a first operative element (e.g. 44A, 44B, MA, and/or MB) may comprise a mechanical element, an electrically conductive element, a visual element, a fluidic element, or other element providing a function associated with operation and/or use of an elongate element, such as a lead. In some examples, the first operative element may comprise a combination of mechanical, electrical, fluidic, etc. properties. The first operative element may be passive in some examples and may be active in some examples. In some examples, the first operative element (e.g. 44A, 44B, MA, and/or MB) may comprise a seal element. In some examples, the zone in which the seal elements (e.g. both 44A, 44B or both MA, MB) are present upon full insertion of a lead into an insertion hole (e.g. 16, 20) may sometimes be referred to as a sealing zone or seal zone. In some examples, the first operative element may comprise an electrically conductive pin, ring (e.g. an annular ring), etc. for establishing electrical communication between the elongate element (e.g. lead) and electrically conductive elements within the header (e.g. first portion) and/or circuitry within a body (e.g. second portion) of an electronic medical device (e.g. IPG 10).

In some examples, while the above-described first operative element (e.g. 44A, 44B, 54A, 54B) is shown in at least FIGS. 1A-4 as being at a proximal end of the elongate elements 40, 50, it will be understood that in some examples the same or similar operative element(s) 44A, 44B, 54A, and/or 54B may be located at or adjacent to an opposite distal end 42B, 52B of the elongate elements 40, 50 (in addition to those elements at the proximal end 42A, 42B). For instance, in some examples one or both of the elongate elements 40, 50 may comprise a lead for sensing physiologic information and/or for electrical stimulation of nerves, muscles, and/or other tissues. In some such examples, a first operative element (e.g. 44A, 44B, 54A, and/or 54B) adjacent the distal end 42B, 52B may comprise a cuff electrode or other type of electrode at the distal end 42B, 52B, which is opposite the proximal end 42A, 52A being connected to the medical device. Such electrodes may be used for sensing and/or for stimulation, and such electrodes may number fewer or greater than the two elements shown for elements 44A, 44B or 54A, 54B. In some examples, one elongate element (40 or 50) may be used for sensing while the other elongate element (40 or 50) may be used for stimulation. In some examples, both elongate elements 40, 50 may be used for the same purpose (e.g. sensing, stimulation) or both elongate elements 40, 50 may be used for multiple purposes (e.g. both sensing and stimulation).

As previously described, in some examples one or both of the elongate elements 40, 50 may comprise a catheter for fluid delivery when the medical device comprises a fluid delivery device (e.g. drug pump, other), and as such the distal end 42B, 52B of the catheter may comprise fluid port(s) for releasing fluids into a patient's body or onto the patient's body.

Figure 5:
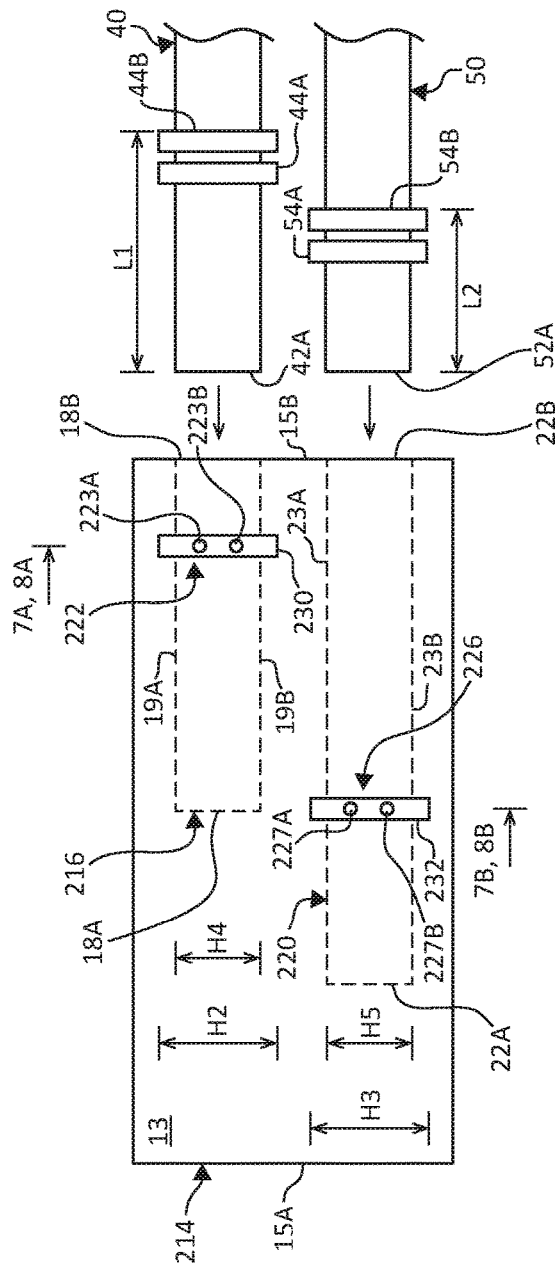
FIG. 5 is a side plan view schematically representing an example medical device and an example elongate element for insertion into a portion of the example medical device.

FIG. 5 is a side plan view schematically representing a first portion 214 of an example medical device 200 and example elongate elements (e.g. 40, 50) for insertion into the first portion 214. In some examples, the first portion 214 of medical device 200 comprises a header (e.g. 14 in FIGS. 1-4) of an implantable medical device, such as an implantable generator, implantable pulse generator, etc. In some examples, at least the first portion 214 of the medical device 200 comprises at least some of substantially the same features and attributes as the first portion 14 of the electronic medical device 20 as previously described in association with at least FIGS. 1A-4, except further comprising vent 222 and vent 226. Each vent 222, 226 provides a fluid communication pathway (e.g. air pathway) from the insertion hole 16, 20 to the external surface of the first portion 214. As further described later in association with at least FIG. 6, the vents 222, 226 may provide air or gas pressure relief during insertion of an elongate element (40, 50) into the respective insertion holes 216, 220.

It will be understood that, in some examples, such vents 222, 226 may be implemented in an example medical device which comprises a non-electronic medical device.

In some examples, as shown in FIG. 5, vent 222 may comprise two apertures 223A, 223B although in some examples, vent 222 may comprise a single aperture or more than two apertures. Similarly, vent 226 may comprise two apertures 227A, 227B although in some examples, vent 226 may comprise a single aperture or more than two apertures.

In some examples, the vents 222, 226 are located separately from the respective position indicators 230, 232. In other words, the vents 222, 226 are not formed in association with the respective position indicators 230, 232.

Figure 6:
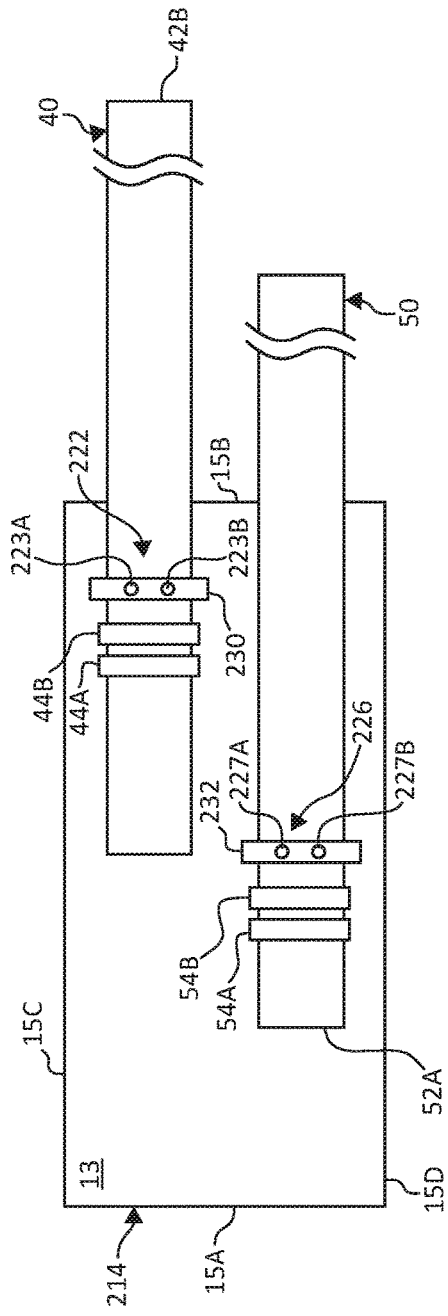
FIG. 6 is a side plan view schematically representing an example medical device with the example elongate element of FIG. 3 inserted into a portion of the example medical device.
Figure 7A:
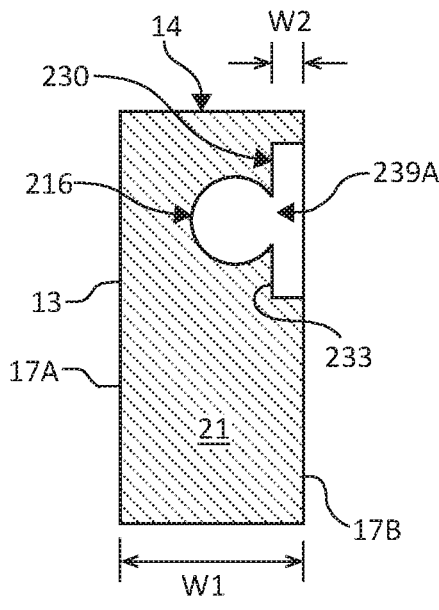
FIGS. 7A-7B are each an enlarged partial sectional view of a first portion of an example medical device.
Figure 7B:
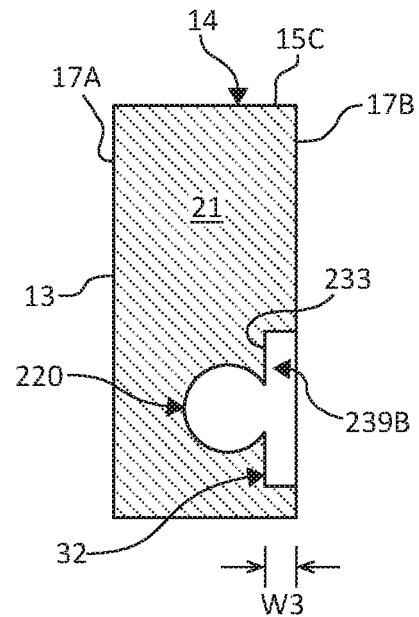

FIGS. 7A and 7B schematically represent example vents 239A, 239B, respectively, one example configuration of vents 222, 226 of FIGS. 5-6. As shown in the enlarged sectional views FIGS. 7A, 7B, in some examples each position indicator 230, 232 is formed as a recess 233, which directly intersects with the respective insertion holes 216, 220, to thereby establish example vents 239A, 239B, respectively. In this arrangement, vent 239A and vent 239B each may act as a larger single vent instead of two smaller vents 223A, 223B forming vent 222 (FIG. 5) or two smaller vents 227A, 227B forming vent 226 (FIG. 5), respectively. In some examples, the recess 233 may partially intersect with the respective insertion holes 216, 220 to establish vents 239A, 239B.

Figure 8A:
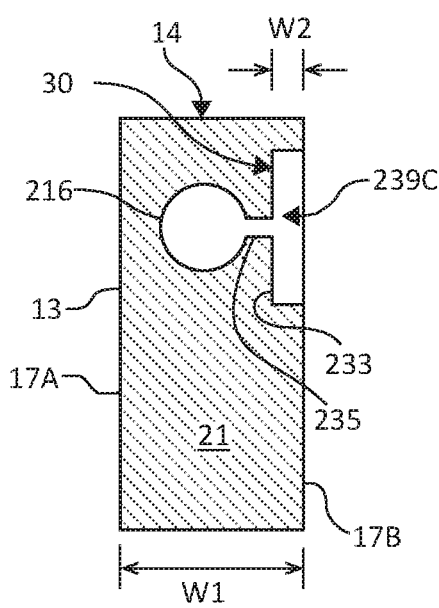
FIGS. 8A-8B are each an enlarged partial sectional view of a first portion of an example medical device.
Figure 8B:
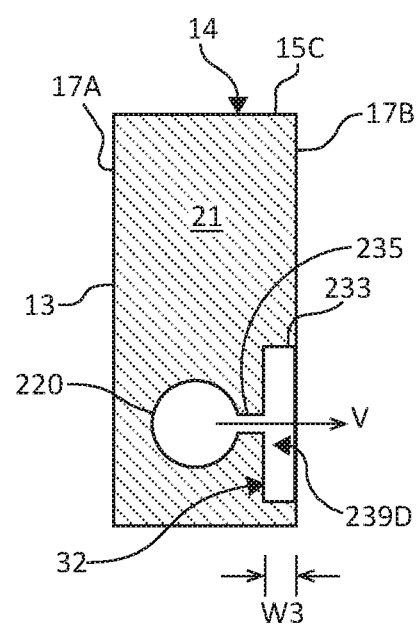

As shown in FIGS. 8A, 8B, in some examples each position indicator 230, 232 (FIG. 5) is formed as a recess 233 with each example vent 239C, 239D being formed as a conduit 235 extending between the respective insertion holes 216, 220 and the recess 233 of the respective position indicators 230, 232. In this arrangement, each vent 239C and vent 239D may provide a single larger vent or be arranged as two smaller vents which are side-by-side but independent of each other.

As represented by the directional arrow V in FIG. 8B, any one of the vents shown in FIGS. 5, 7A, 7B, 8A, 8B provide a pathway for air or gas pressure to escape insertion hole (e.g. 216, 220) to the environment external to the first portion 214 (e.g. header).

With further reference to FIG. 5, in the absence of vents 222, 226 the insertion of the respective elongate elements 40, 50 into the respective insertion holes 216, 220 may sometimes result in air or gas being trapped and compressed within the respective insertion holes 216, 220 due to the sealing action by seals 44A, 44B, and 54A, 54B, respectively. However, the presence of the example vents 222, 226 enables the air under pressure (arising from insertion of elongate elements 40, 50 and that otherwise may be trapped) in the insertion holes 216, 220 to escape to the environment immediately external to the first portion 214. In one aspect, this arrangement may ease insertion of elongate elements 40, 50 and/or enhance their robust securement within the respective insertion holes 216, 220.

In some examples, the respective example vents 222, 226 of FIGS. 5-8B define air passageways which are unrestricted by any valves, membranes, etc. In one aspect, this arrangement may provide gas pressure relief while still maintaining electrically conductive elements of the insertion hole (e.g. 216, 220) and elongate element 40, 50 in a sealed environment. In particular, by locating the vents 222, 226 proximal to the seals 44A, 44B and 54A, 54B (FIG. 5) in some examples, any potential entry of liquids into insertion holes 216, 220 through vents 222, 226 would occur only after the respective elongate elements 40, 50 are completely, properly seated in insertion holes 216, 220 (prior to finalizing implantation of the electronic medical device). Accordingly, any potential liquid intrusion would be excluded by the seals (e.g. 44A, 44B, 54A, 54B).

However, in some examples, each example vents 222, 226 may comprise a one-way flow element (e.g. one-way valve, one-way membrane, etc.) to allow air to exit through the vent 222, 226 but prevent intrusion of liquids from the body or other fluids. In some such examples, the vents 222, 226 may be located distal to the seals 44A, 44B and 54A, 54B while still preventing liquid intrusion into the insertion holes 216, 220.

FIG. 6 is a side plan view schematically representing an example electronic medical device 200 with the example elongate elements 40, 50 of FIG. 5 inserted into a first portion 214 of the example electronic medical device 200. As shown in FIG. 6, in addition to the function of vents 222, 226 during insertion of elongate elements 40, 50, the position indicators 230, 232 provide confirmation of complete or sufficient insertion of elongate elements 40, 50 into the respective insertion holes 216, 220, thereby providing assurance of a proper electro-mechanical connection of the elongate elements 40, 50 to conductive elements within the insertion hole 216, 220 of first portion 214.

With respect to at least FIG. 6, it will be understood that in some examples the vents 222, 226 are generally representative of any of the example vents described and illustrated in association with FIGS. 5, 7A, 7B, 8A, 8B.

Figure 9:
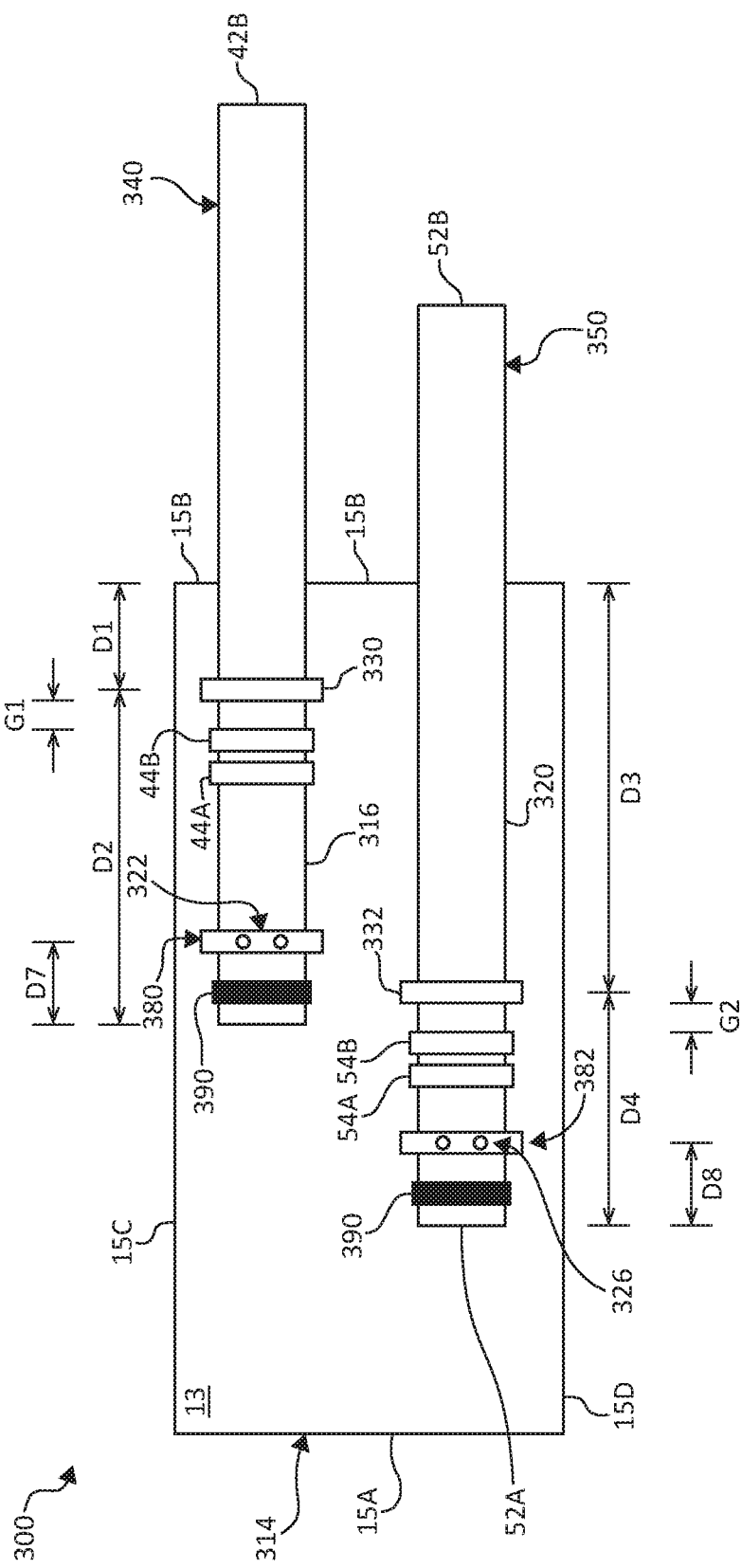
FIG. 9 is a side plan view schematically representing an example medical device with the example elongate element of FIG. 3 inserted into a portion of the example medical device.

FIG. 9 is a side plan view schematically representing an example first portion 314 (e.g. header) of an electronic medical device 300 with elongate elements 340, 350 already inserted into respective insertion holes 316, 320. In some examples, the first portion 314 may comprise at least some of substantially the same features and attributes as the first portion 214 in FIGS. 5-8B, except locating a position indicator 380 distal to the seals 44A, 44B of lead 40 when fully inserted in insertion hole 316 and a position indicator 382 distal to the seals 54A, 54B of lead 50 when fully inserted in insertion hole 320. In some examples, each respective position indicator 380, 382 includes vents 322, 326 to permit gas pressure relief during insertion of the respective elongate elements 40, 50. In some examples, each vent 322, 326 comprises, or is associated with, a one-way valve, one-way membrane, etc. to allow air to exit through the vent 322, 326 but to prevent the intrusion of liquids from the body or other fluids into the sealed area distal to seals 44A, 44B and 54A, 54B, respectively.

In addition to the position indicators 380, 382 including vents 322, 326, the position indicators 380, 382 are located to be visually juxtaposed, upon complete insertion of elongate elements 340, 350, to a visible element 390 of the respective elongate elements 340, 350, to thereby provide confirmation of a complete or proper insertion of the elongate elements 340, 350 within the respective insertion holes 316, 320. In some such examples, the position indicators 380, 382 are located to be proximal to the visible element 390 of elongate elements 340, 350 upon their complete insertion within the respective insertion holes 316, 320. In some examples, element 390 comprises an electrically conductive element which becomes positioned for electrical connection to corresponding electrically conductive element(s) within an interior portion of the insertion holes 316, 320 (not shown for illustrative simplicity), which in turn may be in electrical communication with a second portion of the electronic medical device comprising circuitry or other electrically conductive elements.

It will be understood that in some examples, other arrangements and combinations of the various seals, position indicators, and vents may be implemented based on the foregoing description and illustrations.

In some examples, the visible elements 390 in FIG. 9 may represent and comprise any operative element 390, whether active or passive, such as a mechanical element, an electrical element, an electro-mechanical element, a fluidic element, and/or a seal, etc. In each case, the operative element 390 of the elongate element would be visible through the translucent material of the first portion 314 and therefore could be visualized relative to the position indicator 380, 382, which was visible as a protrusion or recess on the external surface of the header 314 (e.g. first portion) in at least some examples. In some examples, the operative element 390 may sometimes be referred to as a visible element or vice versa.

With regard to any of the vents described in association with FIGS. 5-9, whether or not the vents (e.g. 222, 226, etc.) form part of a position indicator, in some examples at least some of the respective vents may be located according to the following parameters. For instance, in some examples a vent and/or position indicator may be located at a point within one-quarter of a length of the insertion hole 16 or 20 as measured starting from the closed end (e.g. 18A in insertion hole 16 or 22A in insertion hole 20). In some examples, this distance may be represented by identifiers D7 or D8 in FIG. 9. In some examples a vent and/or position indicator may be located at a point (a distance D7 or D8) within one-half of a length of the insertion hole 16 or 20, as measured starting from the closed end (e.g. 18A in insertion hole 16 or 22A in insertion hole 20). In some examples a vent and/or position indicator may be located at a point (a distance D7 or D8) within three-quarters of a length of the insertion hole 16 or 20, as measured starting from the closed end (e.g. 18A in insertion hole 16 or 22A in insertion hole 20).

In some examples, a vent and/or position indicator may be located at a point (e.g. distance D7 or D8) no more than ten percent of the length of the insertion hole 16 or 20, as measured starting from the closed end (e.g. 18A in insertion hole 16 or 22A in insertion hole 20). In some examples, a vent and/or position indicator may be located at a point (D7 or D8) no more than five percent of the length of the insertion hole 16 or 20, as measured starting from the closed end (e.g. 18A in insertion hole 16 or 22A in insertion hole 20). In some examples, a vent and/or position indicator may be located at a point (D7 or D8) no more than two percent of the length of the insertion hole 16 or 20, as measured starting from the closed end (e.g. 18A in insertion hole 16 or 22A in insertion hole 20).

Figure 10:
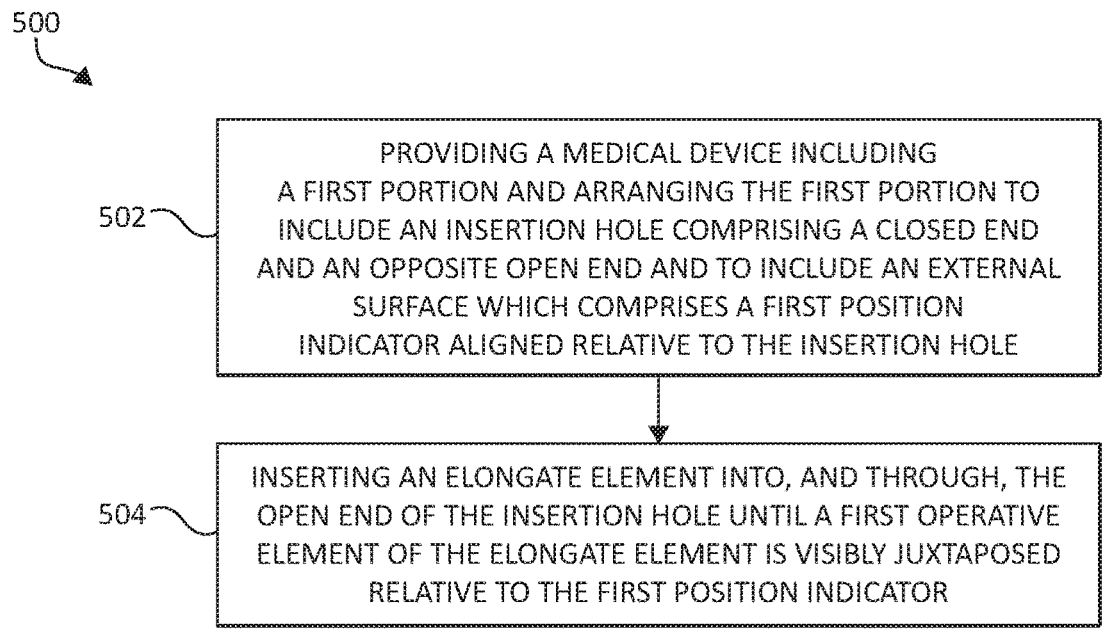
FIG. 10 is a flow diagram schematically representing an example method involving a position indicator for insertion of an elongate element in a first portion of a medical device.

FIG. 10 is a flow diagram schematically representing an example method 500. In some examples, method 500 may be performed via at least some of the medical devices, headers, insertion holes, position indicators, and/or elongate elements (e.g. leads, catheters, other), etc. as previously described in association with FIGS. 1-9. In some examples, method 500 may be performed via medical devices, headers, insertion holes, position indicators, and/or elongate elements (e.g. leads, catheters, other) etc. other than those previously described in association with FIGS. 1-9.

As shown at 502 in FIG. 10, in some examples method 500 comprises providing a medical device including a first portion and arranging the first portion to include an insertion hole comprising a closed end and an opposite open end, with the first portion including an external surface which comprises a first position indicator aligned relative to the insertion hole. In some examples, the first position indicator may have an elongate shape aligned perpendicular to a length of the insertion hole. In some examples, the first position indicator may extend across a longitudinal axis of the insertion hole. In some examples, the first position indicator may have an alignment orientation other than perpendicular relative to the length of the insertion hole.

In some examples, as shown at 504, method 500 comprises inserting an elongate element into, and through, the open end of the insertion hole until a first operative element of the elongate element is visibly juxtaposed relative to the first position indicator. In some examples, the first operative element may sometimes be referred to as the first visible element regardless of the structure and/or function of the first operative element.

Figure 11:
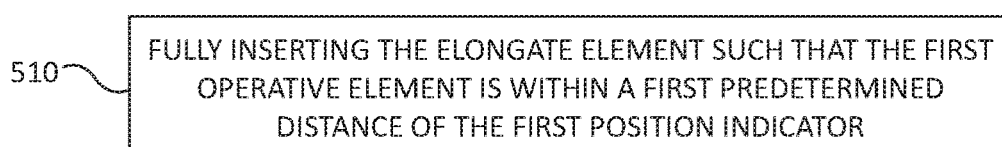
FIGS. 11-12B are each a flow diagram schematically representing an example method involving a position indicator for insertion of an elongate element.

As shown at 510 in FIG. 11, in some examples method 500 may further comprise fully inserting the elongate element into the insertion hole such that the first operative element is within a first predetermined distance of the first position indicator.

Figure 12A:
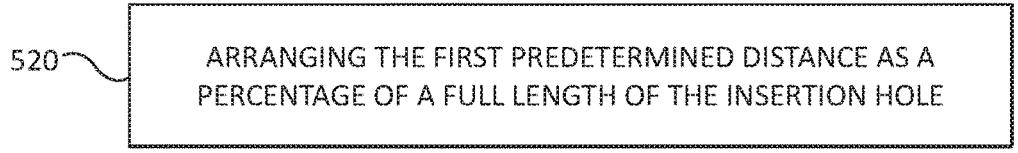

As shown at 520 in FIG. 12A, in some examples method 500 comprises arranging the first predetermined distance as a percentage of a full length of the insertion hole. In some such examples, the first predetermined distance comprises no more than ten percent of a length of the insertion hole. In some examples, the first predetermined distance comprises no more than five percent of a length of the insertion hole. In some examples, the first predetermined distance comprises no more than two percent of a length of the insertion hole. In some such examples, this first predetermined distance may be represented by identifier, such as gaps G1 and/or G2 in FIG. 4 and/or FIG. 9.

In some further examples, the first position indicator may be located within 25 percent, 50 percent, or 75 percent of the full length of the insertion hole, as measured starting from the closed end of the insertion hole. In some examples, this measurement may be represented by distance identifier D2 and/or D4 in FIG. 4 and/or FIG. 9, and/or may be represented by distance identifier D7 and/or D8 in FIG. 9.

Figure 12B:
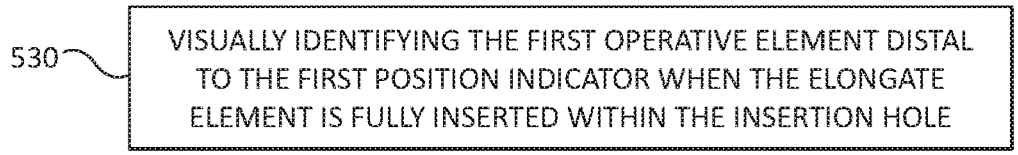

As shown at 530 in FIG. 12B, in some examples, method 500 may further comprise visually identifying the first operative element distal to the first position indicator when the elongate element is fully inserted within the insertion hole. In some examples, the visual identification may be performed with the first operative element located proximal to the first position indicator when the lead is fully inserted within the insertion hole.

FIGS. 13A-13D are each a flow diagram schematically representing an example method 541, which may comprise one example implementation of the method 500 as previously described in association with at least FIGS. 10, 11, 12A, and/or 12B. In some examples, as shown at 540 in FIG. 13A, method 541 comprises arranging the medical device as an electronic medical device and the elongate element as an electrically conductive lead such that full insertion of the lead into the insertion hole establishes at least electrical communication between the electronic medical device and the electrically conductive lead.

As shown at 550 in FIG. 13B, in some examples method 541 may further comprise arranging the electronic medical device as a monitoring device and the lead as a sensing lead.

As shown at 560 in FIG. 13C, in some examples method 541 may further comprise arranging the electronic medical device as a stimulation device and the lead as a stimulation lead.

As shown at 570 in FIG. 13D, in some examples method 541 may further comprise arranging the medical device as a fluid delivery device and the elongate element as a catheter such that proper and/or full insertion of the catheter into the insertion hole established at least fluid communication (and connection) between the fluid delivery device and the catheter.

As shown at 602 in FIG. 14 in some examples the methods 500, 541 described in association with at least FIGS. 10-12B and FIGS. 13A-13D may further comprise a method 600 of arranging a vent between an insertion hole in a first portion of a medical device and an aperture at the external surface of the first portion. In some examples, the method 600 as shown at 602 in FIG. 14 may be performed via at least some of the medical devices, headers, insertion holes, position indicators, vents, and/or elongate elements (e.g. leads, catheters, other), methods etc. as previously described in association with FIGS. 1A-13D. In some examples, the method 600 as shown at 602 in FIG. 14 may be performed via medical devices, headers, insertion holes, position indicators, vents, and/or elongate elements (e.g. leads, catheters, other), methods etc. other than those previously described in association with FIGS. 1A-13D. In some examples, a vent may comprise a plurality of different vents. In some examples, each vent may comprise a plurality of apertures and/or conduits, or each vent may comprise a single aperture and/or single conduit in some examples.

As shown at 604 in FIG. 15, in some examples method 600 may further comprise forming the aperture as part of the first position indicator on the external surface of the first portion of the medical device, such as but not limited to the examples shown in at least FIGS. 5-8B.

As shown at 610 in FIG. 16, in some examples method 600 may further comprise forming the vent as a direct intersection between an insertion hole of the first portion of the medical device and an aperture, which forms part of a first position indicator on the external surface of the first portion. In some such examples, the first position indicator comprises arranging the first position indicator as a recess in which the aperture is formed. In some examples, the vent may be formed via a partial intersection between the insertion hole and the aperture.

As shown at 615 in FIG. 17, in some examples method 600 may further comprise forming the vent as a conduit extending from an insertion hole within a first portion of a medical device to an aperture, which forms part of a first position indicator on the external surface of the first portion. In some examples, at 615 method 600 may further comprise arranging the conduit as a plurality of separate conduits.

As shown at 620 in FIG. 18, in some examples method 600 may further comprise locating the vent within a predetermined distance from the closed end of the insertion hole. In some examples, the predetermined distance may comprise one-quarter of the length of the insertion hole (e.g. as measured starting from the closed end of the insertion hole). In some examples, the predetermined distance may comprise one-half of the length of the insertion hole. In some examples, the predetermined distance may comprise three-quarters of the length of the insertion hole.

With further reference to at least FIG. 18, in some examples at 620 method 600 may further comprise arranging a vent and/or position indicator to be located at predetermined distance, from the closed end of the insertion hole, which is no more than ten percent of the full length of the insertion hole. In some examples, method 600 may further comprise arranging a vent and/or position indicator to be located at a predetermined distance, from the closed end of the insertion hole, no more than five percent of the full length of the insertion hole. In some examples, method 600 may further comprise arranging a vent and/or position indicator to be located at a point, from the closed end of the insertion hole, no more than two percent of the length of the insertion hole.

As shown at 625 in FIG. 19, in some examples method 600 may further comprise locating the vent proximal to a sealing zone within the insertion hole. In some examples, such a sealing zone may correspond to a location in which seal elements (e.g. 44A, 44B or 54A, 54B) are located after a lead is fully inserted within an insertion hole. As shown at 630 in FIG. 20, in some examples method 600 may further comprise locating the vent distal to a sealing zone within the insertion hole.

As shown at 635 in FIG. 21, in some examples method 600 may further comprise arranging the vent to include a one-way flow element, such as but not limited to, the one-way valve, one-way membrane, etc. as previously described in association with at least FIGS. 5-9.

As shown at 640 in FIG. 22, in some examples method 500 and/or method 600 may comprise forming the first position indicator to have the same color as the translucent material from which the first portion is formed. Accordingly, in some examples the first position indicator does not have a color different from the color of the first portion.

As shown in 645 in FIG. 23, in some examples method 500 and/or method 600 may comprise forming the first position indicator (and any additional position indicators) solely by an absence of, or an addition of, the same material from which the first portion was formed. In some examples, the first position indicator may be formed via the addition of a second material different from a first material which forms the first portion, but with the second material having the same color and/or appearance as the first material.

Figure 24:
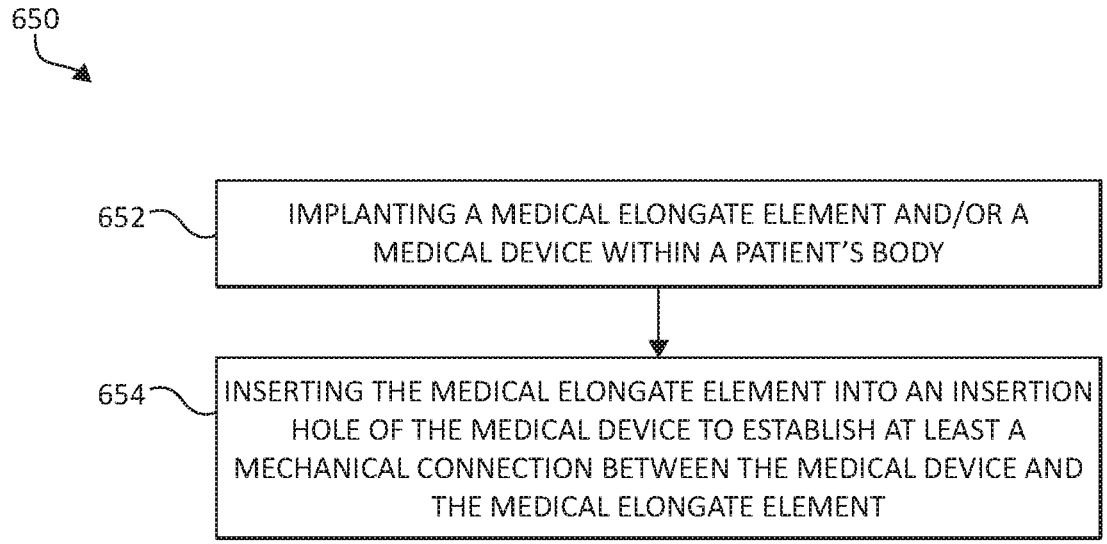
FIGS. 24-26 are each a flow diagram schematically representing an example method regarding implanting an elongate element and/or medical device.

FIG. 24 is a flow diagram schematically representing an example method 650. In some examples, method 650 may be performed via at least some of the medical devices, headers, insertion holes, position indicators, vents, elongate elements (e.g. leads, catheters, other), methods, etc. as previously described in association with FIGS. 1-23. In some examples, method 650 may be performed via medical devices, headers, insertion holes, position indicators, vents, elongate elements (e.g. leads, catheters, other), methods, etc. other than those previously described in association with FIGS. 1-23.

As shown at 652 in FIG. 24, in some examples method 650 comprises implanting a medical elongate element and/or a medical device within a patient's body. As shown at 654 in FIG. 24, in some examples method 650 comprises inserting the medical elongate element into an insertion hole of the medical device to establish at least a mechanical connection between the medical device and the medical elongate element. Via the use of position indicators (e.g. 30, 32 in FIG. 1A), it can be confirmed that a proper and/or full insertion of the medical elongate element was made, thereby confirming that a robust mechanical connection was established. As further shown at 662 in FIG. 26, in some examples method 650 may further comprise establishing an electrical, mechanical, and/or fluidic connection between the medical device and the medical elongate element.

Figure 25:
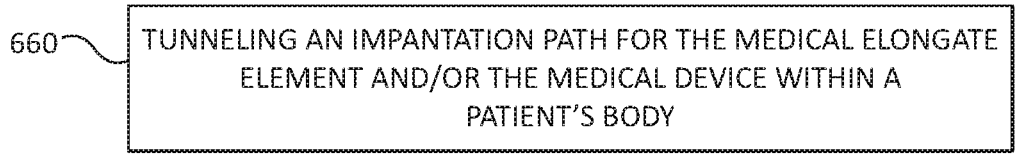
Figure 26:
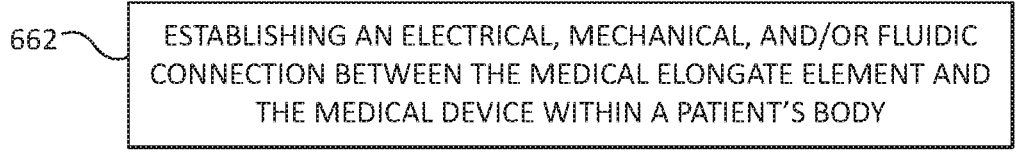

In some examples, as shown at 660 in FIG. 25, method 650 further comprises tunneling an implantation path for the medical elongate element and/or the medical device within the patient's body. In some such examples, the tunneling is performed prior to establishing a mechanical, electrical, and/or fluidic connection between the medical elongate element and the medical device.

Figure 27:
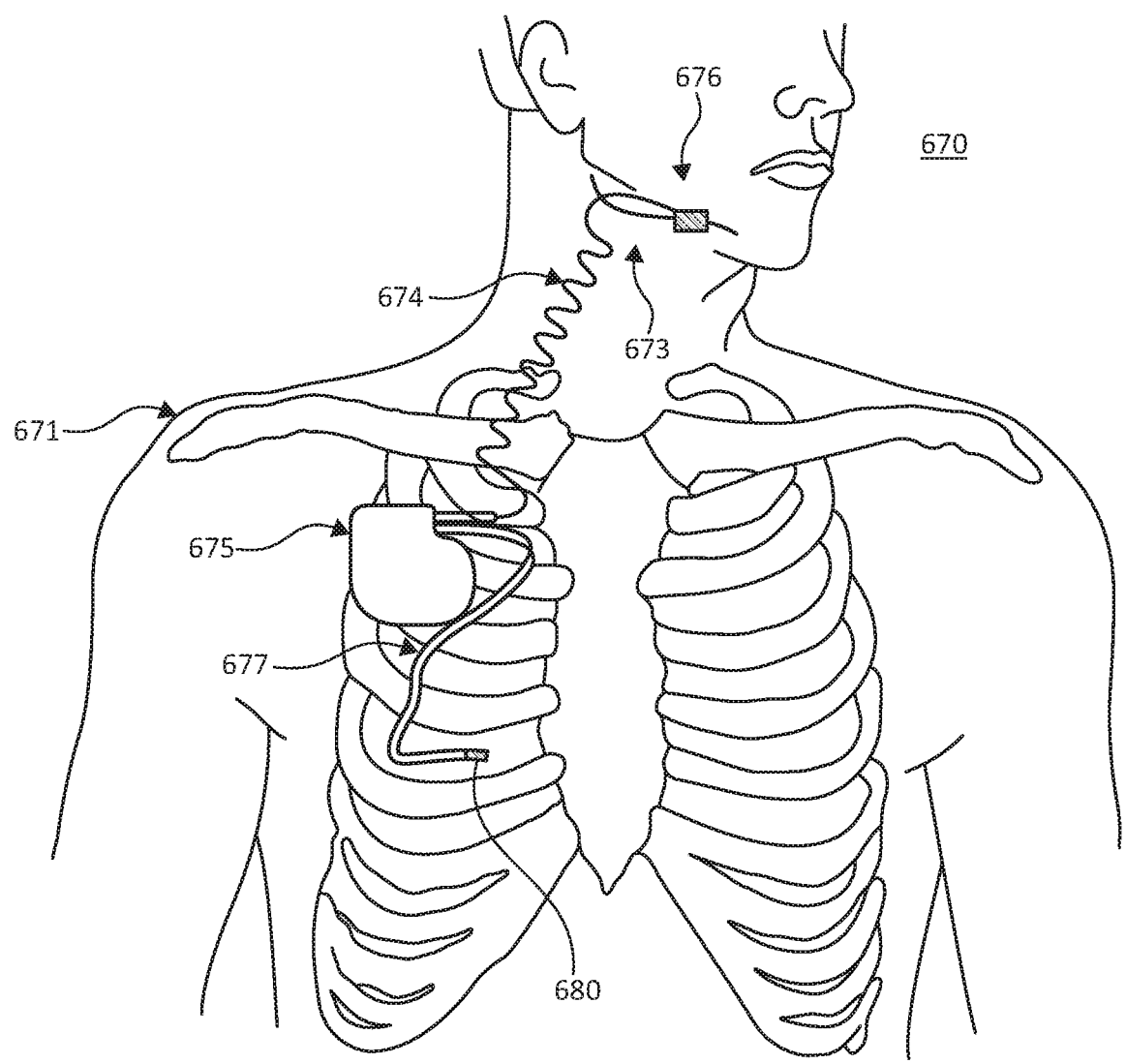
FIG. 27 is a diagram schematically representing an example method of implanting an example medical device and elongate elements and/or an example system of an implantable medical device and implantable elongate elements.

FIG. 27 is a diagram schematically representing an example method 670 of implanting a medical device. In some examples, method 670 comprises one example implementation of method 650 as described in association with at least FIG. 24, FIG. 25, and/or FIG. 26, and/or one example implementation of at least some of the various examples previously described in association with FIGS. 1-23.

As illustrated in FIG. 27, in some examples method 670 comprises surgically positioning medical device 675 within a patient's body 671. In some such examples, medical device 675 is implanted within a pectoral region, although medical device 675 may be implanted elsewhere within the body 671. In some examples, a first elongate element 674 and/or second elongate element 677 also may be implanted within body 671 in which subcutaneously tunneling is typically performed to place the respective elongate elements in their desired positions within the body 671. After such tunneling, the respective elongate elements 674, 677 may be connected to the medical device 675 according to at least some examples of establishing a mechanical, electrical, and/or fluidic connection between the medical device 675 and the elongate elements 674, 677 as described in association with at least FIGS. 1A-26.

In some examples, elongate element 677 may comprise a sensor lead while elongate element 674 may comprise a stimulation lead. In some examples, medical device 675 may comprise an electronic medical device, such as but not limited to, an implantable pulse generator (IPG) for at least performing sleep apnea monitoring, therapy, diagnosis, among other physiologic-related functions. In some examples, medical device 675 may comprise additional or other structures, and perform additional or other functions, as previously described in association with the examples of at least FIGS. 1-26.

In some examples, the elongate element 674 includes a stimulation element 676 (e.g. electrode portion, such a cuff electrode) and extends from the medical device 675 so that the stimulation element 676 is positioned in contact with a desired nerve 673 to stimulate nerve 673 for restoring upper airway patency. In some examples, the desired nerve comprises a hypoglossal nerve. In some instances, a body of the elongate element 674 may sometimes be referred to as being interposed between, and extending between the medical device 675 and the stimulation element 676.

In some examples, device 675 comprises includes at least one sensor portion 680 (electrically and mechanically coupled to the medical device via elongate element 677) positioned in the patient's body 671 for sensing physiologic conditions, such as but not limited to, respiratory effort.

In some examples, the sensor portion 680 detects respiratory effort including respiratory patterns (e.g., inspiration, expiration, respiratory pause, etc.). In some examples, this respiratory information is employed to trigger activation of stimulation element 676 to stimulate a target nerve 673. Accordingly, in some examples, the IPG 675 receives sensor waveforms (e.g. one form of respiratory information) from the respiratory sensor portion 680, thereby enabling the IPG 675 to deliver electrical stimulation according to a therapeutic treatment regimen in accordance with examples of the present disclosure.

In some examples, the sensing and stimulation system for treating sleep disordered breathing (such as but not limited to obstructive sleep apnea) is a totally implantable system which provides therapeutic solutions for patients diagnosed with obstructive sleep apnea. In other examples, one or more components of the system are not implanted in a body of the patient. Whether partially implantable or totally implantable, in some examples the system is designed to stimulate an upper-airway-patency-related nerve during some portion of the repeating respiratory cycle to thereby prevent obstructions or occlusions in the upper airway during sleep.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A medical device comprising:
a first portion comprising:
a first insertion hole to removably receive a first connector portion of a medical elongate element, the first insertion hole comprising a closed end and an opposite open end;
an external surface which comprises a first position indicator, wherein the first position indicator is positioned to be visibly juxtaposed relative to a first operative element of the medical elongate element when the medical elongate element is fully inserted in the first insertion hole, including a gap defined between the first operative element and the first position indicator when the medical elongate element is fully inserted in the first insertion hole.

2. The medical device of claim 1, wherein the medical device comprises an implantable electronic medical device and the elongate element comprises a lead including at least one electrically conductive element, and wherein the lead optionally comprises at least one of a sensing lead and a stimulation lead.

3. The medical device of claim 1, wherein the elongate element comprises a catheter and the medical device comprises a fluid delivery device such that insertion of the catheter into the insertion hole establishes at least fluidic connection between the fluid delivery device and the catheter, and wherein the fluid delivery device optionally comprises a drug pump device.

4. The medical device of claim 1, wherein the first position indicator comprises a recess.

5. The medical device of claim 1, wherein the first position indicator comprises a protrusion.

6. The medical device of claim 1, wherein the first position indicator is located proximal to at least one sealing element of an elongate element upon full insertion of the elongate element into the first insertion hole.

7. The medical device of claim 1, wherein the first portion is made of a translucent material, and wherein the first position indicator comprises the same color as the translucent material from which the first portion is formed.

8. The medical device of claim 1, wherein the first position indicator is defined solely by an absence of, or addition of, the same material from which the first portion was formed.

9. The medical device of claim 1, wherein the external surface of the first portion comprises a second position indicator to be visibly juxtaposed relative to a second operative element of the elongate element when the elongate element is fully inserted in the first insertion hole, and optionally both of the first and second position indicators comprise at least one of a recess and a protrusion.

10. The medical device of claim 1, wherein the first operative element comprises an electrically conductive element.

11. The medical device of claim 10, comprising:
a second portion comprising circuitry to which the electrically conductive element of the elongate element is to be in electrical communication via the first portion.

12. The medical device of claim 1, wherein the first operative element comprises at least one seal element.

13. The medical device of claim 1, wherein the first portion comprises a second insertion hole separate from, and independent of, the first insertion hole, wherein the second insertion hole is to receive a second elongate element, and wherein the external surface of the first portion comprises a second position indicator to be visibly juxtaposed relative to a first operative element of the second elongate element when the second elongate element is fully inserted in the second insertion hole.

14. The medical device of claim 1, comprising:
a vent extending through the first portion between the insertion hole and an aperture exposed at the external surface of the first portion.

15. The medical device of claim 14, wherein the aperture comprises part of the first position indicator.

16. The medical device of claim 15, wherein the first position indicator comprises a recess in which the aperture is formed.

17. The medical device of claim 16, wherein the vent directly intersects with the recess of the insertion hole.

18. The medical device of claim 14, wherein the vent is located at a distance, as measured from the closed end of the insertion hole, within one-quarter of the full length of the insertion hole.

19. The medical device of claim 1, wherein the first position indicator is located between the respective closed and open ends of the first insertion hole, and wherein the first position indicator has a location no more than about one-quarter of a length of the first insertion hole from the closed end of the first insertion hole.

20. The medical device of claim 1, comprising at least one of:
the first position indicator being located at generally the same position as at least one sealing element of an elongate element upon complete insertion of the elongate element into the first insertion hole; and the first position indicator being located proximal to at least one sealing element of an elongate element upon full insertion of the elongate element into the first insertion hole.

21. The medical device of claim 1, wherein an extent of the gap is visually perceptible from an exterior of the first portion.

22. The medical device of claim 1, wherein the medical elongate element extends from a first end opposite a second end, and further wherein the first operative element defines a first edge opposite a second edge with the first edge facing the first end and the second edge facing the second end, and even further wherein the first position indicator defines a first side opposite a second side, and even further wherein when the medical elongate element is fully inserted in the first insertion hole, the first edge of the first operative element faces the closed end of the insertion hole, the second edge of the first operative element faces the first side of the first position indicator and the gap is defined between the second edge and the first side.

23. The medical device of claim 22, wherein when the medical elongate element is fully inserted in the first insertion hole, the first end of the medical elongate element is inside the first insertion hole and the second end is outside of the first portion, and further wherein the first operative element serves as a visually perceptible marker along a length of the medical elongate element, and even further wherein when the medical elongate element is fully inserted in the first insertion hole, the medical elongate element is characterized by the absence of an additional visually perceptible marker between the first operative element and the first position indicator.

24. The medical device of claim 1, wherein the first portion includes a body defining the first insertion hole and the external surface, and further wherein the body and the first position indicator exhibit the same visible light transmission property selected from the group consisting of transparent and translucent.

* * * * *